United States Patent [19]

Nishiwaki et al.

[11] Patent Number: 4,893,214
[45] Date of Patent: Jan. 9, 1990

[54] CAPACITANCE TYPE SENSITIVE ELEMENT AND A MANUFACTURING METHOD THEREOF

[75] Inventors: Satoru Nishiwaki, Tokyo; Yukinobu Takahashi; Kouji Murakami, both of Yokohama; Norisuke Fukuda, Tokyo, all of Japan

[73] Assignee: Kabushiki Kaisha Toshiba, Kawasaki, Japan

[21] Appl. No.: 242,201

[22] Filed: Sep. 9, 1988

[30] Foreign Application Priority Data

Sep. 29, 1987 [JP] Japan ................. 62-242586

[51] Int. Cl.$^4$ .................. H01G 7/00; H01G 5/20
[52] U.S. Cl. ...................... 361/286; 29/25.42
[58] Field of Search .......... 73/336.5; 29/25.42; 361/286

[56] References Cited

U.S. PATENT DOCUMENTS

| 4,164,868 | 8/1979 | Suntola | 73/336.5 |
| 4,393,434 | 7/1983 | Imai et al. | 361/286 |
| 4,438,480 | 3/1984 | Chambaz et al. | 73/336.5 X |
| 4,632,879 | 12/1986 | Tamaka et al. | 73/336.5 X |

FOREIGN PATENT DOCUMENTS

| 8703095 | 5/1987 | Int'l Pat. Institute . | |
| 57-3905 | 1/1982 | Japan . | |
| 60-253958 | 12/1985 | Japan . | |
| 2126350 | 3/1984 | United Kingdom . | |
| 2133161 | 7/1984 | United Kingdom . | |
| 2136130 | 9/1984 | United Kingdom . | |
| 2149922 | 6/1985 | United Kingdom | 361/286 |

*Primary Examiner*—Donald A. Griffin
*Attorney, Agent, or Firm*—Foley & Lardner, Schwartz, Jeffery, Schwaab, Mack, Blumenthal & Evans

[57] ABSTRACT

A capacitance type sensitive element comprises a pair of electrode pairs formed on an insulating substrate and having opposite electrode faces perpendicular or slantingly formed with respect to a face of the insulating substrate; and a sensing material disposed between the opposite electrode faces of the electrodes and having electrical characteristics changed on the basis of the physical or chemical interaction between the sensing material and a substance to be detected.

A method for manufacturing a capacitance type sensitive element comprises the steps of forming a groove on an insulating substrate; forming a metallic thin film having a predetermined thickness on the insulating substrate having the groove; performing the etching of a predetermined pattern in a portion including a bottom face portion of the groove in the metallic thin film, and forming a pair of electrodes; coating the entire surface of the pair of electrodes and the insulating substrate with a humidity sensitive material, and thereafter hardening the coated humidity sensitive material; and patterning the hardened humidity sensitive material.

A method for manufacturing a capacitance type sensitive element may comprise the steps of forming a metallic thin film having a predetermined thickness on an insulating substrate; patterning the metallic thin film and forming a pair of electrodes at a predetermined distance; coating the entire surface of the insulating substrate including a pair of electrodes with a humidity sensitive material, and thereafter hardening the coated humidity sensitive material; and patterning the hardened humidity sensitive material.

9 Claims, 6 Drawing Sheets

CAPACITANCE TYPE SENSITIVE ELEMENT AND A MANUFACTURING METHOD THEREOF

The present invention relates to a capacitance type sensitive element and a manufacturing method thereof for detecting humidity, etc. using sensing bodies having electrical characteristics of dielectric constant changed due to an external factor such as humidity, etc.

BACKGROUND OF THE INVENTION

Conventionally, a sensitive element is manufactured by using sensing bodies having electrical characteristics of dielectric constant changed by a physical or chemical interaction between the sensing bodies and an external factor such as humidity, etc. to be detected.

FIG. 1 shows a first conventional example of such a sensitive element. In this sensitive element, a lower electrode 32, a sensitive thin film 33 composed of a humidity sensing high polymer, and an upper electrode 34 are sequentially stacked on an insulating substrate 31 such as glass, constituting a sensitive portion 35 composed of a capacitor with the sensitive thin film 33 as a dielectric. The external factor such as humidity to be detected is absorbed to the sensitive thin film 33 through the upper electrode 34, and is discharged through the upper electrode 34 so that the upper electrode 34 is formed by a very thin metallic evaporation thin film having a thickness of several hundred angstroms to provide conductivity and permeability of moisture, etc. Further, one end side of the upper electrode 34 extends downwards onto the upper face of the insulating substrate 31 in a stepped portion at an end edge of the sensitive thin film 33, forming a connecting pad 34a for connecting the upper electrode 34 to a detecting circuit. Reference numeral 32a is a connecting pad on the side of the lower electrode 32.

The external factor such as humidity, etc. to be detected is absorbed to the sensitive thin film 33, and the change in dielectric constant, i.e., the change in capacitance between the upper electrode 34 and the lower electrode 32 is outputted to detect the humidity as a change in electrical signal by the detecting circuit.

However, in the above first conventional example, since the upper electrode 34 is formed by the metallic evaporation after the formation of the sensitive thin film 33 composed of a humidity sensing high polymer, the sensitive thin film 33 is heated in the evaporation and a thermal reaction or other reaction is caused between the sensitive thin film 33 and the metal for the upper electrode 34 stacked by the evaporation, causing deterioration on a surface of the sensitive thin film 33. Also, since the upper electrode 34 is formed by a very thin metallic evaporation thin film having a thickness of several hundred angstroms, dispersion is caused with respect to permeability of moisture and conductivity, so that the electrical characteristics of the elements tend to be dispersed. Further, since the upper electrode 34 is formed by the very thin metallic evaporation as mentioned above, the thin film tends to be broken in the stepped portion at the end edge of the sensitive thin film 33 in the evaporation, thereby lowering the yield in manufacture and reducing the reliability.

FIG. 2 shows a second conventional example of the sensitive element. In this conventional example, two lower electrodes 37 and 38 are disposed on an insulating substrate 31 at a suitable distance, and a sensitive thin film 39 and an upper electrode 40 are sequentially stacked on the two lower electrodes 37 and 38. One capacitor is formed by the one lower electrode 37 and the upper electrode 40 with the sensitive thin film 39 as a dielectric, and another capacitor is formed by the other lower electrode 38 and the upper electrode 40, so that a sensitive portion 41 is constructed by the two capacitors connected in series to each other.

Even in the second conventional example, similar to the first conventional example, the external factor such as humidity, etc. to be detected is absorbed or discharged with respect to the sensitive thin film 39 through the upper electrode 40 Therefore, the upper electrode 40 is formed by a very thin metallic evaporation thin film having a thickness of several hundred angstroms. Accordingly, even in the second conventional example, a thermal reaction or other reaction is caused between the sensitive thin film 39 and the metal in the evaporation of the metal for the upper electrode 40 so that a surface of the sensitive thin film 39 might be deteriorated, and dispersion is caused with respect to the permeability of moisture and conductivity so that the electrical characteristics of the elements tend to be dispersed.

As mentioned above, in the first conventional example, the upper electrode is formed by the metallic evaporation after the formation of the sensitive thin film, a thermal reaction or other reaction is caused between the sensitive thin film and the metal in the evaporation, so that a surface of the sensitive thin film might be deteriorated. Also, since the upper electrode is formed by a very thin film having a thickness of several hundred angstroms, dispersion is caused with respect to the permeability of moisture and conductivity, and the electrical characteristics of the elements tend to be dispersed. Further, the upper electrode tends to be broken in a stepped portion at an end edge of the sensitive thin film in the evaporation, thereby reducing the yield in manufacture and reliability.

In the second conventional example, since the upper electrode is formed by a very thin metallic evaporation thin film having a thickness of several hundred angstroms, similarly to the first conventional example, a surface of the sensitive thin film might be deteriorated at the manufacturing time thereof, and dispersion is caused with respect to the permeability of moisture and conductivity and the electrical characteristics of the elements tend to be dispersed.

Further, in another sensitive element, the electrical characteristics of the sensitive element are deteriorated by hysteresis characteristics and the speed in response is low, and a humidity sensitive material having a thermally low resistance cannot be used to avoid the deterioration of the sensitive thin film. Further, in the conventional manufacturing processes of the humidity sensitive element, it is necessary to perform a process for forming the upper electrode and a patterning process of the humidity sensitive thin film, thereby simplifying the processes.

SUMMARY OF THE INVENTION

To overcome the problems mentioned above, an object of the present invention is to provide a capacitance type sensitive element and a manufacturing method thereof in which it is not necessary to dispose an upper electrode and a surface of a sensitive thin film is not deteriorated in a process thereof after the formation of the sensitive thin film, and dispersion with respect to the electrical characteristics between elements is prevented and the electrode at the manufacturing time is prevented from being broken, thereby improving the yield in manufacture and reliability.

With the above object in view, the present invention resides in a capacitance type sensitive element comprising electrode pair means formed on an insulating substrate and having opposite electrode faces perpendicular or slantingly formed with respect to a face of the insulating substrate; and sensing means disposed between the opposite electrode faces of the electrode pair means and having electrical characteristics changed on the basis of the physical or chemical interaction between the sensing means and a substance to be detected.

A method for manufacturing a capacitance type sensitive element comprises the steps of forming a groove on an insulating substrate; forming a metallic thin film having a predetermined thickness on the insulating substrate having the groove; performing the etching of a predetermined pattern in a portion including a bottom face portion of the groove in the metallic thin film, and forming a pair of electrodes; coating the entire surface of the pair of electrodes and the insulating substrate with a humidity sensitive material, and thereafter hardening the coated humidity sensitive material; and patterning the hardened humidity sensitive material.

A method for manufacturing a capacitance type sensitive element may comprise the steps of forming a metallic thin film having a predetermined thickness on an insulating substrate; patterning the metallic thin film and forming a pair of electrodes at a predetermined distance; coating the entire surface of the insulating substrate including the pair of electrodes with a humidity sensitive material, and thereafter hardening the coated humidity sensitive material; and patterning the hardened humidity sensitive material.

BRIEF DESCRIPTION OF THE DRAWINGS

The present invention will be more apparent from the following description of the preferred embodiments thereof in conjunction with the accompanying drawings in which.

DETAILED DESCRIPTION OF THE PREFERRED EMBODIMENTS

The preferred embodiments of the present invention will now be described with reference to the accompanying drawings.

Figure 1:
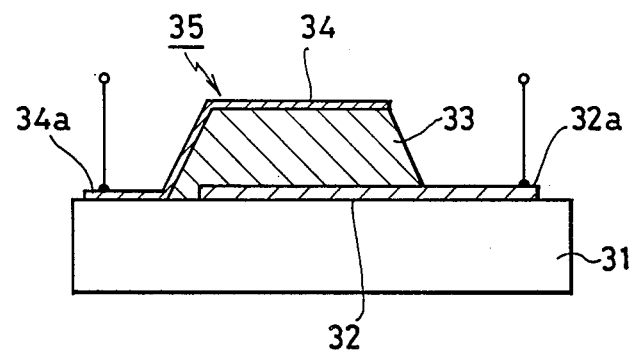
FIG. 1 is a longitudinally cross-sectional view showing a first conventional example of a sensitive
Figure 2:
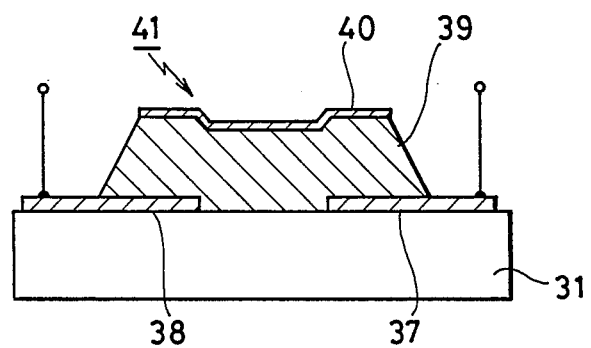
FIG. 2 is a longitudinally cross-sectional view showing a second conventional example of the sensitive element.
Figure 3:
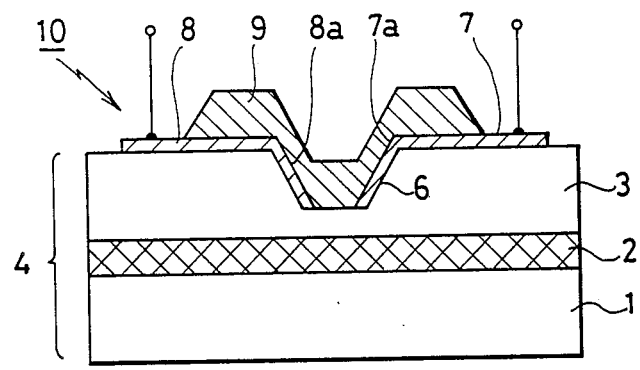
FIG. 3 is a longitudinally cross-sectional view showing a sensitive element in accordance with an embodiment of the present invention.
Figure 4A:
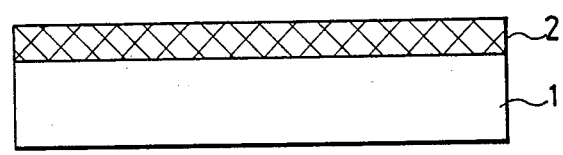
FIGS. 4A to 4G are views showing an example of manufacturing processes of the sensitive element in the embodiment of the present invention.
Figure 4:
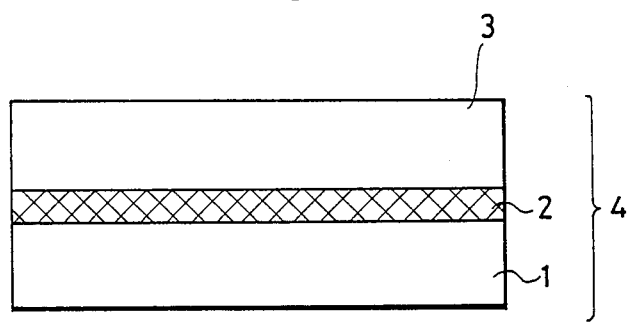
Figure 4:
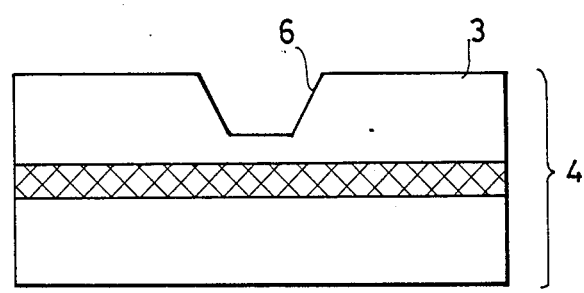
Figure 4:
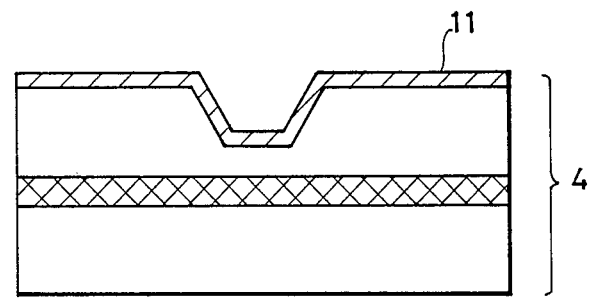
Figure 5:
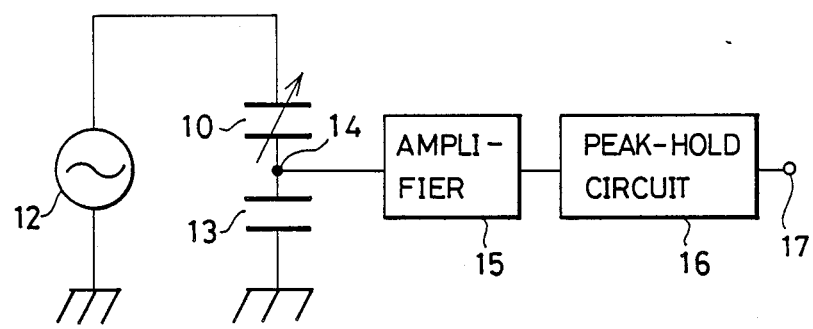
FIG. 5 is a circuit diagram showing an embodiment of a detecting circuit applied to the embodiment of the present invention.

FIGS. 3 to 5 show a capacitance type sensitive element in accordance with an embodiment of the present invention. In this embodiment, dielectric constant in a sensing body is changed by humidity to be detected.

In the construction of a capacitance type sensitive element 10 shown in FIG. 3, a silicon oxide thin film 2 is formed by oxidizing a surface of a silicon substrate 1, and a silicon nitride thin film 3 is stacked on the silicon oxide thin film 2 by CVD method at a predetermined thickness, constituting an insulating substrate 4. A recessed groove 6 is disposed in a predetermined position of the silicon nitride thin film 3 and has opposite inner wall faces having an angle approximately perpendicular to a face of the insulating substrate 4. A pair of metallic electrodes 7 and 8 are formed from the opposite inner wall faces to an upper face portion of the insulating substrate 4, and opposite electrode faces 7a and 8a are formed in portions of the opposite inner wall faces.

A sensing body 9 composed of a humidity sensing high polymer is disposed on the electrodes 7 and 8, and a sensing portion composed of a capacitor is constituted by the sensing body 9 as a dielectric on the opposite electrode faces 7a and 8a.

The preferred embodiment of the manufacturing processes of the sensing element will now be described in detail with reference to FIGS. 4A to 4G.

A surface of the silicon substrate 1 is oxidized and the silicon oxide thin film 2 is formed thereon as shown in FIG. 4A, and the silicon nitride thin film 3 is stacked on the silicon oxide thin film 2 by CVD method at a predetermined thickness, constituting the insulating substrate 4 as shown in FIG. 4B. The recessed groove 6 has opposite inner wall faces having an angle approximately perpendicular to the upper surface of the insulating substrate 4 and is disposed in a predetermined position of the silicon nitride thin film 3 by selective etching as shown in FIG. 4C. Next, a metallic thin film 11 is stacked on the insulating substrate 4 by sputtering method at a predetermined thickness.

Figure 4E:
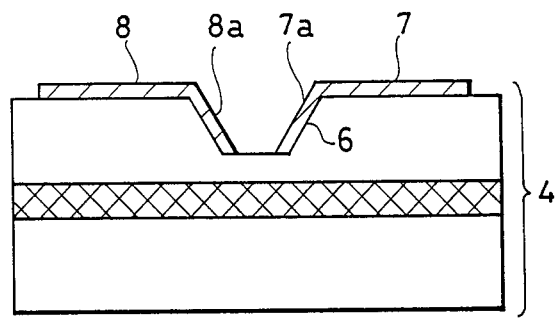
Figure 4F:
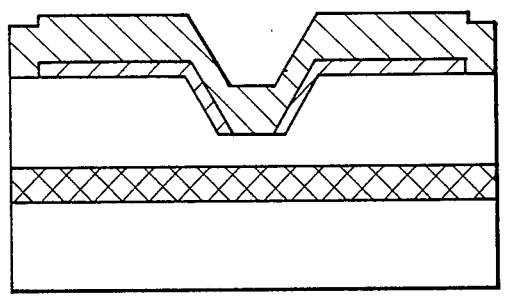
Figure 4G:
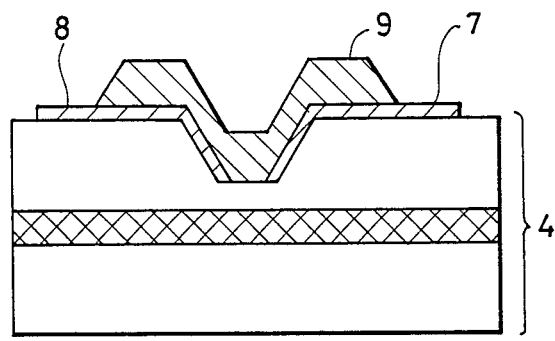

Etching of a predetermined pattern including the etching of a portion of a bottom wall face of the groove 6 is then performed in the metallic thin film 11, forming the pair of electrodes 7 and 8 as shown in FIG. 4E. Next, the entire surface of the insulating substrate 4 including the electrodes 7 and 8 is coated with a material made of humidity sensing high polymer such as polyimide by spin coating and is thermally hardened as shown in FIG. 4F and is then patterned as shown in FIG. 4G, completing the formation of the sensitive element 10.

In the sensitive element 10 of this embodiment constructed as above, the moisture in the atmosphere to be detected is directly absorbed to the sensing body 9, detecting the humidity of the atmosphere by the change in dielectric constant, i.e., the change in capacitance of the capacitor formed in a portion of the groove 6.

FIG. 5 shows an example of a detecting circuit for outputting the change in capacitance as a change in voltage signal.

In FIG. 5, an oscillator 12 oscillates an alternating current having a constant amplitude at a constant frequency, and the sensing element 10 and a reference capacitor 13 having a constant capacitance are connected in series to each other between both output terminals of the oscillator 12. An amplifier 15 and a peak-hold circuit 16 are sequentially connected to a common connection point 14 between the sensing element 10 and the reference capacitor 13, and an output terminal 17 is connected to the peak-hold circuit 16.

An alternating signal waveform having an amplitude divided to the respective capacitances of the sensing element 10 and the reference capacitor 13 is generated at the common connection point 14. Accordingly, when the sensing element 10 detects the humidity to be detected and the capacitance thereof is changed, the alternating signal waveform having an amplitude in accordance with this change is generated at the common connection point 14. After this signal is amplified suitably by the amplifier 15, its peak value is held by the peak-hold circuit 16, outputting from the output terminal 17 a direct current voltage at a level definitely determined with respect to the humidity and thus detecting the humidity.

Figure 6:
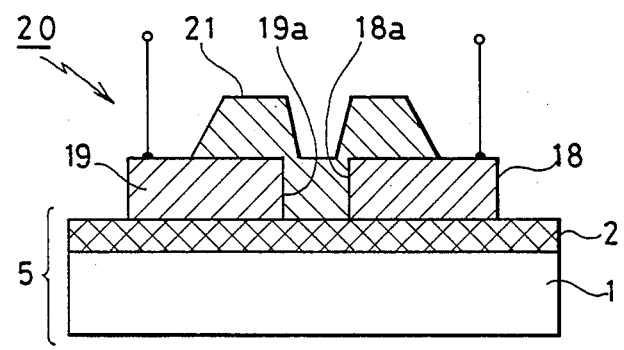
FIG. 6 is a cross-sectional view showing the sensitive element in another embodiment of the present invention.

FIGS. 6 and 7 show another embodiment of the present invention. In this embodiment, the dielectric constant of sensing body is changed by the humidity to be detected.

In a capacitance type sensitive element 20 of this embodiment, two electrodes 18 and 19 having a predetermined sufficient thickness are disposed in parallel to each other and are disposed on an insulating substrate 5 in which a silicon oxide thin film 2 is formed on a silicon substrate 1. Opposite electrode faces 18a and 19a of the electrodes 18 and 19 are formed by opposite side wall faces thereof so as to be perpendicular to the upper face of the insulating substrate 5. A sensing body 21 is embedded between the opposite electrode faces 18a and 19a, constituting a sensing portion composed of capacitors with the sensing body 21 as a dielectric.

The preferred embodiment of the manufacturing processes of the sensing element will next be described in detail with reference to FIGS. 7A to 7E.

Figure 7A:
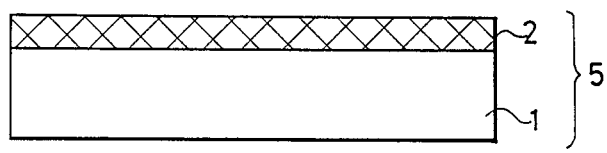
FIG. 7 is a process view showing an embodiment of manufacturing processes of the sensitive element in the another embodiment of the present invention.
Figure 7B:
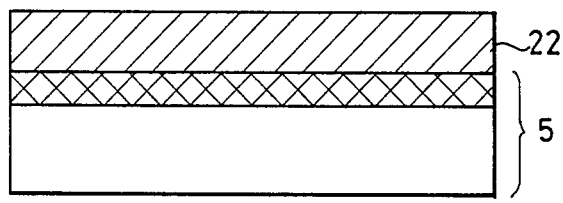
Figure 7C:
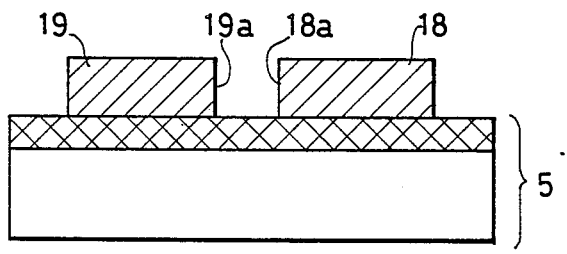
Figure 7D:
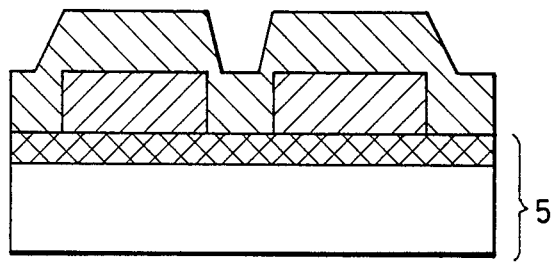
Figure 7E:
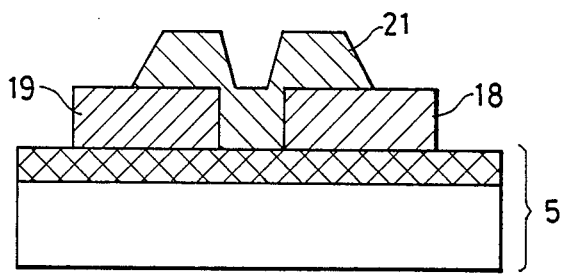

A surface of the silicon substrate 1 is oxidized and the silicon oxide thin film is formed on the oxidized surface of the silicon substrate 1, constituting the insulating substrate 5 as shown in FIG. 7A. An aluminum thin film 22 having a predetermined sufficient thickness is stacked on the insulating substrate 5 by sputtering method as shown in FIG. 7B, and is patterned by selective etching, forming the pair of electrodes 18 and 19 having the opposite electrode faces 18a and 19a at a predetermined distance as shown in FIG. 7C. Next, the entire surface of the insulating substrate 5 including the electrodes 18 and 19 is coated with a material made of humidity sensing high polymer and is thermally hardened as shown in FIG. 7D and is patterned as shown in FIG. 7E, completing the formation of the capacitance type sensitive element 20.

In the sensing element 20 of the embodiment constructed above, the moisture of the atmosphere to be detected is directly absorbed to the sensing body 21, detecting the humidity of the atmosphere by the change in dielectric of the sensing body 21, i.e., the change in capacitance of the capacitors formed in portions of the opposite electrode faces 18a and 19a. When the sensing element 20 is embedded into the detecting circuit of FIG. 5, the humidity can be detected by outputting the change in capacitance thereof as a change in direct current voltage, similar to the first embodiment mentioned above.

In the above embodiments, the silicon oxide thin film is formed on the silicon substrate to form an insulating substrate, but another insulating substrate such as glass substrate may be used. Further, the sensing body may be formed, without using the coating means by spin coating, by dropping another material onto only a portion of the opposite electrode face and hardening the dropped material.

As mentioned above, in accordance with the present invention, a pair of electrodes are formed on the insulating substrate such that opposite electrode faces have an angle perpendicular or approximately perpendicular to a face of the insulating substrate, and a sensing body is disposed between the opposite electrode faces, so that an external factor such as humidity to be detected is directly absorbed by the sensing body and is discharged therefrom. Accordingly, since it is not necessary to dispose the upper electrode formed by a thin metallic evaporation thin film, etc. as in the conventional structure, a surface of the sensing thin film is not deteriorated at a step after the formation of the sensing thin film and dispersion is not caused with respect to the electrical characteristics between the elements caused by the upper electrode. Further, the electrode is prevented from being broken at the manufacturing time thereof and the yield in manufacture and the reliability can be improved.

Also, in the sensing element of the present invention, the electrical characteristics of the sensing element are prevented from being deteriorated by hysteresis characteristics, and the speed in response becomes high, and a sensing thin film material having a thermally low resistance can be used to avoid the deterioration of the sensing thin film. Further, in processes for manufacturing the humidity sensing element in the present invention, it is not necessary to perform a process for forming the upper electrode and a patterning process of the humidity sensing thin film, simplifying the manufacturing processes of the sensing element.

What is claimed is:

1. A capacitance type sensitive element comprising:
a pair of electrodes formed on an insulating substrate and having opposite electrode faces perpendicular or slantingly formed with respect to a face of the insulating substrate; and
sensitive material disposed between the opposite electrode faces of the pair of electrodes and on both of the electrodes and having electrical characteristics changed on the basis of the physical or chemical interaction between the sensing means and a substance to be detected.

2. A capacitance type sensitive element as claimed in claim 1, wherein two electrodes having a predetermined thickness are disposed on the insulating substrate in parallel to each other, and the opposite electrode faces are formed on opposite side wall faces of the two electrodes.

3. A capacitance type sensitive element comprising:
electrode pair means formed on an insulating substrate and having opposite electrode faces perpendicular or slantingly formed with respect to a face of the insulating substrate; and
sensing means disposed between the opposite electrode faces of the electrode pair means and having electrical characteristics changed on the basis of the physical or chemical interaction between the sensing means and a substance to be detected, wherein the electrode pair means is disposed on opposite inner wall faces of a groove disposed in the insulating substrate.

4. A method for manufacturing a capacitance type sensitive element comprising the steps of:
forming a groove on an insulating substrate;

forming a metallic thin film having a predetermined thickness on the insulating substrate having the groove;

performing the etching of a predetermined pattern in a portion including a bottom face portion of the groove in the metallic thin film, and forming a pair of electrodes;

coating the entire surface of the pair of electrodes and the insulating substrate with a humidity sensitive material, and thereafter hardening the coated humidity sensitive material; and patterning the hardened humidity sensitive material.

5. A manufacturing method as claimed in claim 4, wherein the humidity sensitive material is composed of a high polymer material.

6. A manufacturing method as claimed in claim 4, wherein the groove is approximately in the shape of a V.

7. A method for manufacturing a capacitance type sensitive element comprising the steps of:

forming a metallic thin film having a predetermined thickness on an insulating substrate;

patterning the metallic thin film and forming a pair of electrodes at a predetermined distance;

coating the entire surface of the insulating substrate including a portion between the pair of electrodes and a portion on the both of the electrodes with a humidity sensitive material, and thereafter hardening the coated humidity sensitive material; and patterning the hardened humidity sensitive material.

8. A manufacturing method as claimed in claim 7, wherein the humidity sensitive material is composed of a high polymer material.

9. A manufacturing method as claimed in claim 7, wherein the pair of electrodes are spaced apart from each other by vertical opposite wall portions thereof.

* * * * *